United States Patent
Hasegawa

(10) Patent No.: US 9,044,137 B2
(45) Date of Patent: Jun. 2, 2015

(54) WIRELESS COMMUNICATION TERMINAL

(75) Inventor: Yasuhiro Hasegawa, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 200 days.

(21) Appl. No.: 13/489,144

(22) Filed: Jun. 5, 2012

(65) Prior Publication Data

US 2012/0315863 A1  Dec. 13, 2012

(30) Foreign Application Priority Data

Jun. 7, 2011  (JP) ................................ 2011-127279

(51) Int. Cl.
*H04B 5/00* (2006.01)
*A61B 5/00* (2006.01)
*H04B 1/16* (2006.01)
*H04W 52/02* (2009.01)

(52) U.S. Cl.
CPC ............ *A61B 5/0006* (2013.01); *H04B 1/1607* (2013.01); *H04W 52/0229* (2013.01); *H04W 52/028* (2013.01); *A61B 5/0031* (2013.01); *A61B 2560/0209* (2013.01); *A61B 2560/0219* (2013.01); *Y02B 60/50* (2013.01)

(58) Field of Classification Search
CPC ............... A61B 5/0031; A61B 5/6898; G06K 19/0715; G06K 19/0723; G08B 13/2417; H04B 5/0031; H04B 5/0043; H04B 5/0087; H04B 5/02
USPC ........................................................ 455/41.1
See application file for complete search history.

(56) References Cited

U.S. PATENT DOCUMENTS

| | | | |
|---|---|---|---|
| 6,662,052 B1 * | 12/2003 | Sarwal et al. ................... 607/59 |
| 8,140,053 B2 * | 3/2012 | Jatschka et al. ............... 455/410 |
| 8,237,561 B2 * | 8/2012 | Beigel et al. ............... 340/572.1 |
| 8,611,828 B2 * | 12/2013 | Richter et al. ............. 455/67.11 |
| 2003/0078003 A1 * | 4/2003 | Hunter et al. ................... 455/41 |
| 2008/0143531 A1 * | 6/2008 | Tadokoro ................... 340/572.1 |

(Continued)

FOREIGN PATENT DOCUMENTS

| | | |
|---|---|---|
| JP | 2001-197573 A | 7/2001 |
| JP | 2002-014072 A | 1/2002 |
| JP | 2003-144417 A | 5/2003 |

(Continued)

OTHER PUBLICATIONS

Japanese Office Action dated Jan. 20, 2015, issued in corresponding JP Patent Application No. 2011-127279 with English translation (6 pages).

*Primary Examiner* — Lewis West
(74) *Attorney, Agent, or Firm* — Westerman, Hattori, Daniels & Adrian, LLP

(57) ABSTRACT

A wireless communication terminal may include a power supply unit that supplies direct current (DC) power, a wireless communication antenna, a wireless communication module that transmits communication data to an external terminal through the wireless communication antenna, an activation signal output unit that converts an electromagnetic wave received through the wireless communication antenna into DC power, and generates and outputs an activation signal if the converted DC power is greater than or equal to a predetermined power value, and a control unit that performs control such that the DC power is supplied from the power supply unit to the wireless communication module if the activation signal is output from the activation signal output unit.

10 Claims, 6 Drawing Sheets

(56) References Cited

U.S. PATENT DOCUMENTS

| | | | |
|---|---|---|---|
| 2008/0288027 A1* | 11/2008 | Kroll et al. | 607/60 |
| 2009/0135886 A1* | 5/2009 | Robertson et al. | 375/133 |
| 2011/0196452 A1* | 8/2011 | Forsell | 607/60 |
| 2011/0300801 A1* | 12/2011 | Kerselaers | 455/41.1 |
| 2012/0100887 A1* | 4/2012 | Tekin et al. | 455/556.1 |
| 2012/0302874 A1* | 11/2012 | Hollstien | 600/424 |

FOREIGN PATENT DOCUMENTS

| | | |
|---|---|---|
| JP | 2007-193566 A | 8/2007 |
| JP | 2008-200110 A | 9/2008 |
| JP | 2009-205205 A | 9/2009 |

* cited by examiner

WIRELESS COMMUNICATION TERMINAL

BACKGROUND OF THE INVENTION

1. Field of the Invention

The present invention relates to a wireless communication terminal.

Priority is claimed on Japanese Patent Application No. 2011-127279, filed Jun. 7, 2011, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In the medical or healthcare field, approaches have been actively made in which biological data is collected from the surface of the human body or the inside of the body using a terminal with various sensors, the biological data collected by the terminal is transferred to a storage device and stored, and the biological data stored in the storage device is used for health management, disease diagnosis, medical treatment, or the like. For this purpose, when the terminal for transferring biological data is connected with the storage device through a wired cable, the freedom of movement is restricted. Thus, it is desirable to transmit biological data by wireless communication so that the terminal can be freely carried. This need is high in the medical field, particularly, in implantable medical devices.

Generally, an implantable medical device operates by electric power supplied from a battery. Thus, when a battery is depleted and a voltage is lowered, it is necessary to exchange the battery. Surgery is required to exchange a battery of an implantable medical device. In this case, since the burden on a patient is large, and an adverse effect such as an infection may occur, it is desirable to avoid depletion of a battery to the utmost. For this, studies on techniques of generating electric power from vibrations, temperature differences, light, electromagnetic waves, or the like have been conducted. For example, wireless communication systems such as a non-contact integrated circuit (IC) tag system or an IC card system in which a wireless transmitting unit transmitting data and a wireless receiving unit having low power consumption which is disposed separately from the wireless transmitting unit are provided, and the wireless transmitting unit is activated based on an activation signal received by the wireless receiving unit have been known as examples of products in which a wireless communication technique is combined with a technique of generating electric power from an electromagnetic wave (for example, see Japanese Unexamined Patent Application, First Publication No. 2009-205205).

SUMMARY

According to the preferred embodiments of the present invention, a wireless communication terminal capable of activating a wireless communication module when communication is started while reducing power consumption is provided.

A wireless communication terminal may include: a power supply unit that supplies direct current (DC) power; a wireless communication antenna; a wireless communication module that transmits communication data to an external terminal through the wireless communication antenna; an activation signal output unit that converts an electromagnetic wave received through the wireless communication antenna into DC power, and generates and outputs an activation signal if the converted DC power is greater than or equal to a predetermined power value; and a control unit that performs control such that the DC power is supplied from the power supply unit to the wireless communication module if the activation signal is output from the activation signal output unit.

The activation signal output unit may include a rectifying unit that converts the electromagnetic wave into the DC power through rectification, and the activation signal output unit may output the activation signal if the DC power converted by the rectifying unit is greater than or equal to a predetermined value.

The activation signal output unit may further include a filter unit that extracts an electromagnetic wave of a specific frequency band from the electromagnetic wave, and the rectifying unit may rectify the extracted electromagnetic wave of the frequency band.

The activation signal output unit may further include a demodulating unit that demodulates an identifier transmitted by using the electromagnetic wave, and the activation signal output unit may output the activation signal when the identifier demodulated by the demodulating unit is a predetermined identifier.

The demodulating unit may operate by using the DC power converted by the rectifying unit.

The activation signal output unit may further include a demodulating unit that demodulates an identifier transmitted by using the electromagnetic wave, and the activation signal output unit may output the activation signal if the identifier demodulated by the demodulating unit is a predetermined identifier.

The demodulating unit may operate by using the DC power converted by the rectifying unit.

The wireless communication terminal may be a terminal installed inside a body.

The wireless communication terminal may be a terminal installed outside a body.

According to the preferred embodiments of the present invention, an activation signal output unit converts an electromagnetic wave received through a wireless communication antenna into direct current (DC) power, and generates and outputs an activation signal when the converted DC power is greater than or equal to a predetermined power value. A control unit performs control such that the DC power is supplied from the power supply unit to the wireless communication module when the activation signal is output from the activation signal output unit. In other words, when an electromagnetic wave of a predetermined power value or more, which is converted into the DC power, is received, the DC power is supplied from the power supply unit to the wireless communication module. Thus, power consumption can be reduced, and the wireless communication module can be activated when communication is started.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated for explanatory purpose.

First Preferred Embodiment

Figure 1:
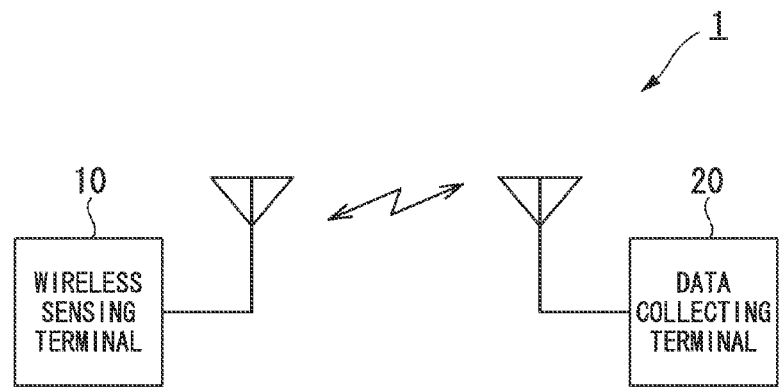
FIG. 1 is a schematic view illustrating a configuration of a biological data monitoring system in accordance with a first preferred embodiment of the present invention.

Hereinafter, a first preferred embodiment of the present invention will be described with reference to the accompanying drawings. FIG. 1 is a schematic view illustrating a configuration of a biological data monitoring system in accordance with the first preferred embodiment of the present invention. The biological data monitoring system 1 includes a wireless sensing terminal 10 and a data collecting terminal 20. The wireless sensing terminal 10 acquires biological data such as blood pressure, pulse, electrocardiograph information, heart rate, oxygen level in the blood, body temperature, glycosuria, or blood glucose level from the surface of the human body or the inside of the body using various sensors. Further, the wireless sensing terminal 10 acquires device status data representing a status of each part included in the wireless sensing terminal 10 using various sensors. Further, the wireless sensing terminal 10 wirelessly transmits the acquired biological data and the device status data to the data collecting terminal 20. The data collecting terminal 20 collects and stores the biological data and the device status data wirelessly transmitted from the wireless sensing terminal 10. The wireless sensing terminal 10 is installed inside the body. The data collecting terminal 20 is installed outside the body.

The first preferred embodiment of the present invention will be described in connection with an example in which the wireless sensing terminal 10 and the data collecting terminal 20 perform wireless communication in a one-to-one manner. However, the present invention can be applied even when the wireless sensing terminal 10 and the data collecting terminal 20 perform wireless communication in a 1-to-N manner, an M-to-1 manner, or an M-to-N manner (N and M are natural numbers).

Figure 2:
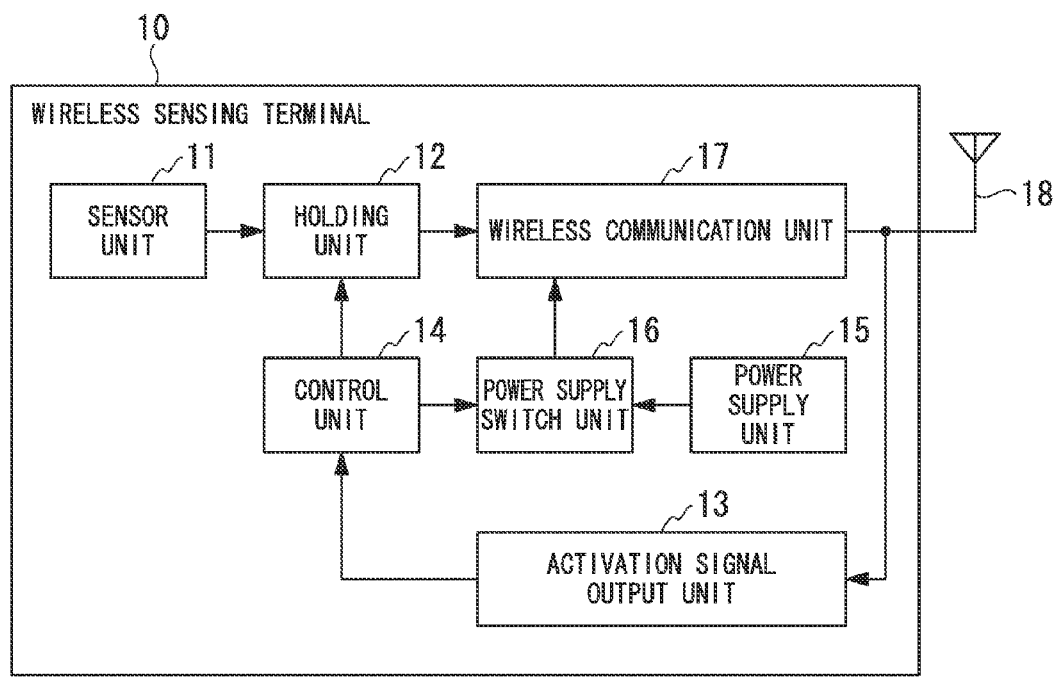
FIG. 2 is a block diagram illustrating a configuration of a wireless sensing terminal in accordance with the first preferred embodiment of the present invention.

Next, a configuration of the wireless sensing terminal 10 will be described. FIG. 2 is a block diagram illustrating a configuration of the wireless sensing terminal 10 in accordance with the first preferred embodiment of the present invention. In the example of FIG. 2, the wireless sensing terminal 10 includes a sensor unit 11, a holding unit 12, an activation signal output unit 13, a control unit 14, a power supply unit 15, a power supply switch unit 16, a wireless communication unit 17 (a wireless communication module), and an antenna 18 (a wireless communication antenna).

The sensor unit 11 is installed on the surface of the human body or in the body, and acquires biological data by sensing, for example, blood pressure, pulse, electrocardiograph information, heart rate, oxygen level in the blood, body temperature, glycosuria, or blood glucose. Further, the sensor unit 11 acquires device status data by sensing a status of each part included in the wireless sensing terminal 10 such as a voltage of the power supply unit 15. Hereinafter, the biological data or the device status data acquired by the sensor unit 11 is referred to as collection data. The sensor unit 11 outputs the collection data to the holding unit 12.

The holding unit 12 acquires and holds the collection data output from the sensor unit 11, and outputs the held collection data to the wireless communication unit 17 under control of the control unit 14. The activation signal output unit 13 receives an electromagnetic wave transmitted from the data collecting terminal 20 through the antenna 18, and generates an activation signal from the received electromagnetic wave. Further, when the activation signal is generated, the activation signal output unit 13 outputs the activation signal to the control unit 14. A detailed configuration of the activation signal output unit 13 will be described later.

When the activation signal is input from the activation signal output unit 13, the control unit 14 controls the holding unit 12 such that the collection data held in the holding unit 12 is output to the wireless communication unit 17. Further, when the activation signal is input from the activation signal output unit 13, the control unit 14 controls the power supply switch unit 16 such that electric power is supplied from the power supply unit 15 to the wireless communication unit 17. Further, after the wireless communication unit 17 completes data transmission, the control unit 14 controls the power supply switch unit 16 such that a supply of electric power from the power supply unit 15 to the wireless communication unit 17 is stopped.

The power supply unit 15 supplies electric power (DC power) to the sensor unit 11, and supplies electric power to the wireless communication unit 17 under control of the power supply switch unit 16. The power supply switch unit 16 controls a supply of electric power from the power supply unit 15 to the wireless communication unit 17 under control of the control unit 14. The wireless communication unit 17 is supplied with electric power from the power supply unit 15 and then activated (starts an operation). Further, the wireless communication unit 17 transmits the collection data input from the holding unit 12 to the data collecting terminal 20 through the antenna 18 using an electromagnetic wave.

Figure 3:
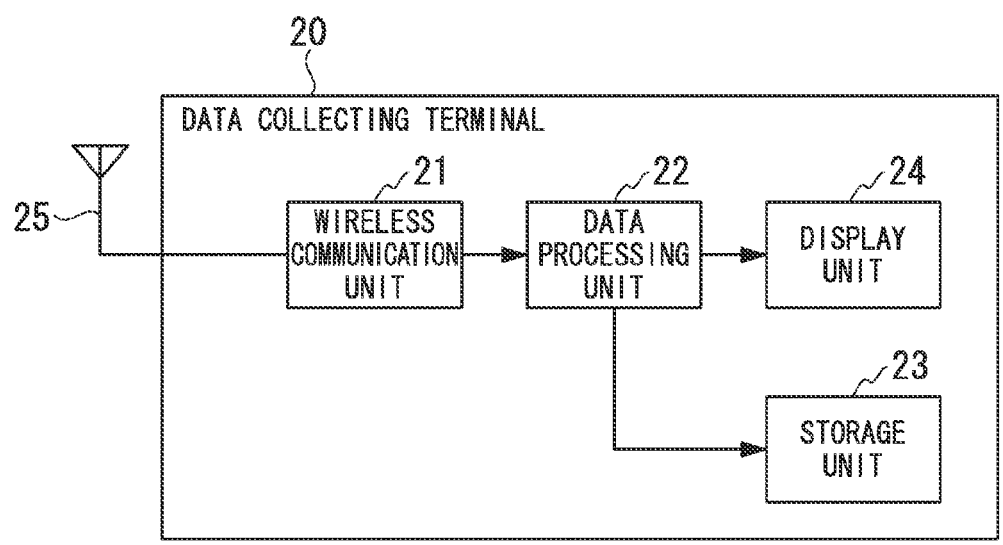
FIG. 3 is a block diagram illustrating a configuration of a data collecting terminal in accordance with the first preferred embodiment of the present invention.

Next, a configuration of the data collecting terminal 20 will be described. FIG. 3 is a block diagram illustrating a configuration of the data collecting terminal 20 in accordance with the first preferred embodiment of the present invention. In the example of FIG. 3, the data collecting terminal 20 includes a wireless communication unit 21, a data processing unit 22a, a storage unit 23, a display unit 24, and an antenna 25.

In order to start reception of the collection data from the wireless sensing terminal 10, the wireless communication unit 21 transmits a data request signal to the wireless sensing terminal 10 through the antenna 25 using an electromagnetic wave. The data request signal may be transmitted to the wireless sensing terminal 10 at an arbitrary timing such as a timing instructed by a user or a predetermined timing.

The wireless communication unit 21 receives the collection data transmitted from the wireless sensing terminal 10 using the electromagnetic wave through the antenna 25, and outputs the received collection data to the data processing unit 22. The data processing unit 22 converts a data format of the collection data input from the wireless communication unit 21 into a storage data format to generate storage data, and outputs the generated storage data to the storage unit 23. Further, the data processing unit 22 converts the collection data input from the wireless communication unit 21 into display data such as text or an image, and outputs the converted display data to the display unit 24. The storage unit 23 stores the storage data input from the data processing unit 22. The display unit 24 displays the display data input from the data processing unit 22. Through this configuration, the data collecting terminal 20 can cause the collection data transmitted from the wireless sensing terminal 10 to be displayed on the display unit 24 and to be stored in the storage unit 23.

Figure 4:
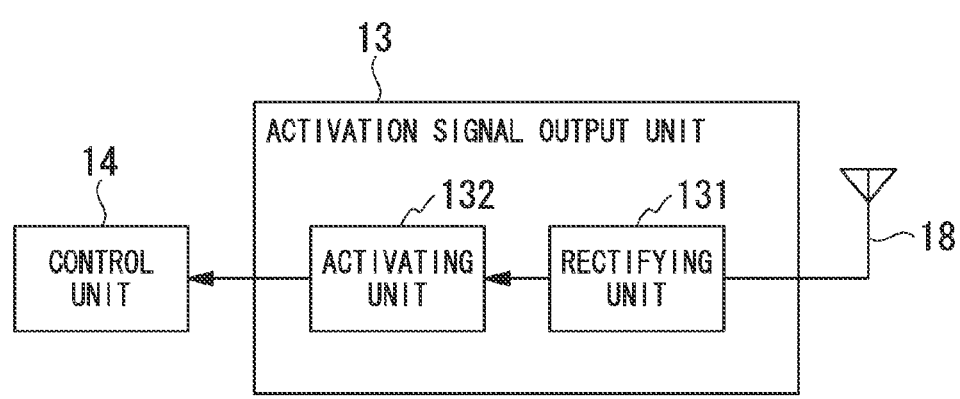
FIG. 4 is a block diagram illustrating a configuration of an activation signal output unit in accordance with the first preferred embodiment of the present invention.

Next, a configuration of the activation signal output unit 13 included in the wireless sensing terminal 10 will be described. FIG. 4 is a block diagram illustrating a configuration of the activation signal output unit 13 in accordance with the first preferred embodiment of the present invention. In the example of FIG. 4, the activation signal output unit 13 includes a rectifying unit 131 and an activating unit 132. The rectifying unit 131 receives the electromagnetic wave transmitted from the data collecting terminal 20 through the antenna 18. Then, the rectifying unit 131 rectifies the received electromagnetic wave to be converted into a DC voltage, and outputs the converted DC voltage to the activating unit 132. The activating unit 132 operates using the DC voltage input from the rectifying unit 131. Further, the activating unit 132 monitors a level of the DC voltage input from the rectifying unit 131, and outputs the activation signal when the DC voltage is greater than or equal to a predetermined threshold value. In this way, when the electromagnetic wave used to transmit the data request signal is received from the data collecting terminal 20, the activation signal output unit 13 outputs the activation signal. The predetermined threshold value may be a fixed value or may be arbitrarily set according to an environment.

As described above, in order to start reception of the collection data from the wireless sensing terminal 10, the data collecting terminal 20 transmits the data request signal to the wireless sensing terminal 10 using the electromagnetic wave. Further, the rectifying unit 131 included in the activation signal output unit 13 of the wireless sensing terminal 10 converts the electromagnetic wave used to transmit the data request signal into the DC voltage through rectification. Further, the activating unit 132 included in the activation signal output unit 13 outputs the activation signal when the DC voltage converted by the rectifying unit 131 is greater than or equal to a predetermined threshold value. Further, when the activating unit 132 outputs the activation signal, the control unit 14 controls the holding unit 12 such that the collection data held in the holding unit 12 is output to the wireless communication unit 17. Further, when the activation signal output unit 13 outputs the activation signal, the control unit 14 controls the power supply switch unit 16 such that electric power is supplied from the power supply unit 15 to the wireless communication unit 17. Further, when the collection data is input from the holding unit 12, the wireless communication unit 17 transmits the collection data to the data collecting terminal 20 through the antenna 18 using the electromagnetic wave using electric power supplied from the power supply unit 15. After the wireless communication unit 17 completes transmission of the collection data, the control unit 14 controls the power supply switch unit 16 such that a supply of electric power from the power supply unit 15 to the wireless communication unit 17 is stopped. When a supply of electric power from the power supply unit 15 is stopped, the wireless communication unit 17 stops its operation.

As described above, the wireless sensing terminal 10 generates the activation signal from the electromagnetic wave, which is used to transmit the data request signal, transmitted from the data collecting terminal 20. Then, the wireless sensing terminal 10 supplies electric power to the wireless communication unit 17 based on the generated activation signal and thereby activates the wireless communication unit 17. Accordingly, the wireless sensing terminal 10 can activate the wireless communication unit 17 when communication is started while further reducing power consumption. Further, since the wireless sensing terminal 10 activates the wireless communication unit 17 when communication is started, power consumption at the time of standby can be reduced, and depletion of the power supply unit 15 can be suppressed.

Second Preferred Embodiment

Next, a second preferred embodiment of the present invention will be described with reference to the accompanying drawings. A biological body monitoring system in accordance with the second preferred embodiment of the present invention includes a wireless sensing terminal and a data collecting terminal similarly to the first preferred embodiment. The second preferred embodiment of the present invention is different from the first preferred embodiment in a configuration of an activation signal output unit included in the wireless sensing terminal. The remaining configuration of the wireless sensing terminal in accordance with the second preferred embodiment of the present invention is the same as in the first preferred embodiment. The data collecting terminal in the second preferred embodiment of the present invention has the same configuration as the data collecting terminal 20 in the first preferred embodiment.

Figure 5:
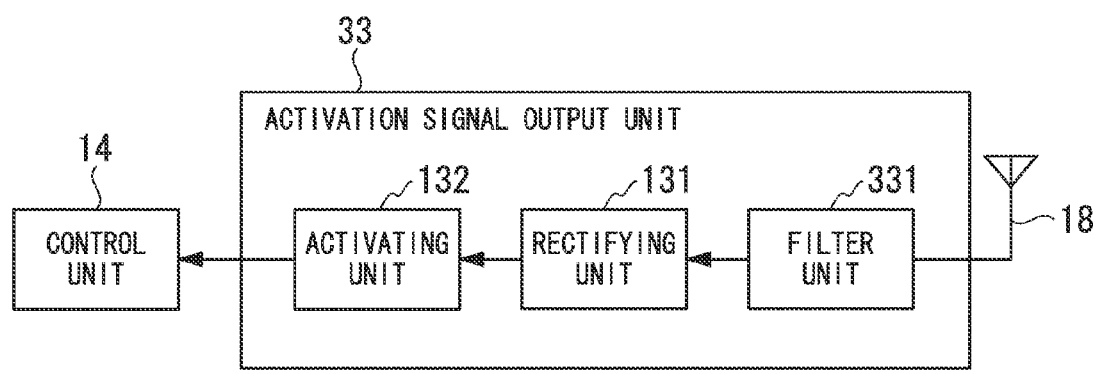
FIG. 5 is a block diagram illustrating a configuration of an activation signal output unit in accordance with a second preferred embodiment of the present invention.

Next, a configuration of an activation signal output unit included in the wireless sensing terminal will be described. FIG. 5 is a block diagram illustrating a configuration of an activation signal output unit 33 in accordance with the second preferred embodiment of the present invention. In the example of FIG. 5, the activation signal output unit 33 includes a filter unit 331, a rectifying unit 131, and an activating unit 132. The filter unit 331 receives electromagnetic waves transmitted from the outside through the antenna 18, and outputs only an electromagnetic wave of a predetermined frequency band among the received electromagnetic waves to the rectifying unit 131. The predetermined frequency band includes a frequency band of an electromagnetic wave, which is used to transmit the data request signal, transmitted from the data collecting terminal. Accordingly, it is possible to prevent an electromagnetic wave transmitted from a terminal other than the data collecting terminal from being input to the rectifying unit 131.

The rectifying unit 131 rectifies the electromagnetic wave input from the filter unit 331 to be converted into a DC voltage, and outputs the converted DC voltage to the activating unit 132. The activating unit 132 is the same as the activating unit 132 in the first preferred embodiment.

As described above, since the activation signal output unit 33 of the wireless sensing terminal includes the filter unit 331, the activation signal output unit 33 can suppress an interference signal or an electromagnetic wave having a frequency band different from a frequency band of the electromagnetic wave used to transmit the data request signal and then output the activation signal for activating the wireless communication unit 17. Thus, when the data collecting terminal is not located nearby, the wireless sensing terminal can prevent the wireless communication unit 17 from being erroneously activated by an interference signal or an electromagnetic wave transmitted from a terminal other than the data collecting terminal, and can further reduce depletion of a battery.

Third Preferred Embodiment

Figure 6:
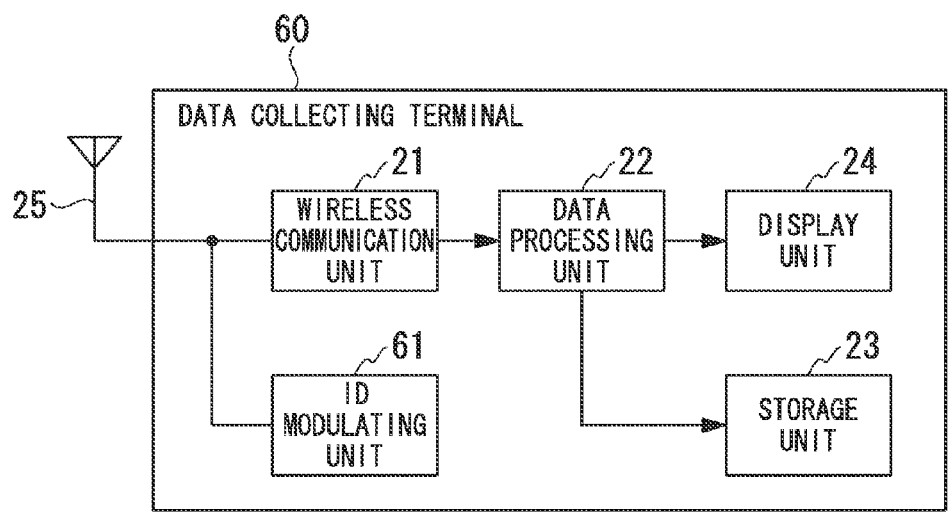
FIG. 6 is a block diagram illustrating a configuration of a data collecting terminal in accordance with a third preferred embodiment of the present invention.

Next, a third preferred embodiment of the present invention will be described with reference to the accompanying drawings. A biological body monitoring system in accordance with the third preferred embodiment of the present invention includes a wireless sensing terminal and a data collecting terminal similarly to the first preferred embodiment. FIG. 6 is a block diagram illustrating a configuration of a data collecting terminal 60 in accordance with the third preferred embodiment of the present invention. In the example of FIG. 6, the data collecting terminal 60 includes a wireless communication unit 21, a data processing unit 22, a storage unit 23, a display unit 24, an antenna 25, and an ID modulating unit 61.

The data processing unit 22, the storage unit 23, the display unit 24, and the antenna 25 are the same as in the first preferred embodiment. In order to start reception of the collection data from the wireless sensing terminal, the wireless communication unit 21 transmits the data request signal to the wireless sensing terminal through the antenna 25 using the electromagnetic wave, and outputs a communication start instruction signal to the ID modulating unit 61. The ID modulating unit 61 receives the communication start instruction signal from the wireless communication unit 21, and modulates ID information (identifier) uniquely specifying the wireless sensing terminal that is a communication partner to generate an ID modulation signal. Then, the ID modulating unit 61 transmits the ID modulation signal to the wireless sensing terminal using the electromagnetic wave having the same frequency band as the electromagnetic wave used to transmit the data request signal through the antenna 25.

Figure 7:
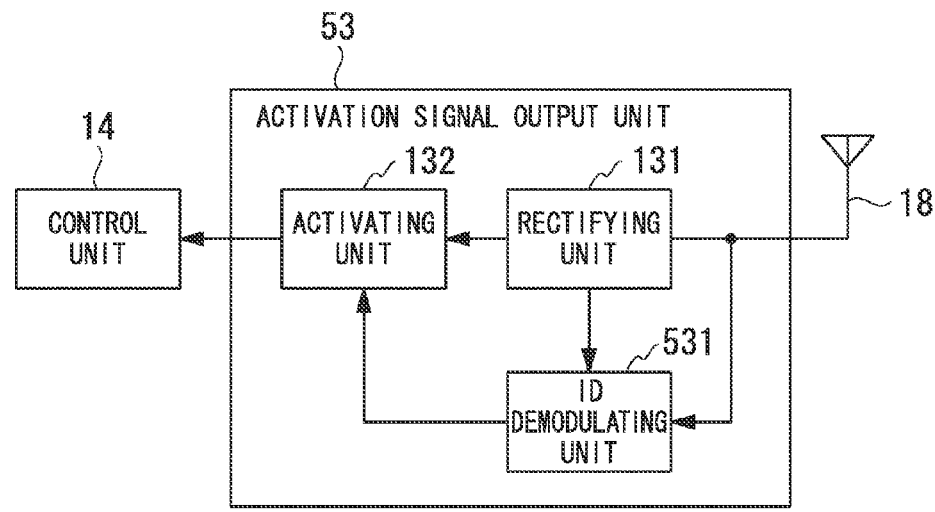
FIG. 7 is a block diagram illustrating a configuration of an activation signal output unit in accordance with the third preferred embodiment of the present invention.

Next, a configuration of an activation signal output unit included in the wireless sensing terminal will be described. FIG. 7 is a block diagram illustrating a configuration of an activation signal output unit 53 in accordance with the third preferred embodiment of the present invention. In the example of FIG. 7, the activation signal output unit 53 includes a rectifying unit 131, an activating unit 132, and an ID demodulating unit 531 (a demodulating unit).

The rectifying unit 131 receives the electromagnetic wave, which is used to transmit ID modulation signal and the data request signal, transmitted from the data collecting terminal 60 through the antenna 18. Then, the rectifying unit 131 rectifies the received electromagnetic wave to be converted into a DC voltage, and outputs the converted DC voltage to the activating unit 132 and the ID demodulating unit 531. The ID demodulating unit 531 operates using the DC voltage input from the rectifying unit 131. The ID demodulating unit 531 receives the ID modulation signal transmitted from the data collecting terminal 60 through the antenna 18. Further, the ID demodulating unit 531 demodulates the received ID modulation signal and acquires ID information. The ID demodulating unit 531 compares the acquired ID information with predetermined ID information uniquely specifying its own terminal. Then, when the two pieces of ID information are found to match each other as a result of a comparison, the ID modulating unit 61 outputs ID matching information representing that the two pieces of ID information match each other to the activating unit 132. However, when the two pieces of ID information are not found to match each other as a result of a comparison, the ID modulating unit 61 does not output the ID matching information.

The activating unit 132 operates using the DC voltage input from the rectifying unit 131. Further, when the ID matching information is input from the ID modulating unit 61, the activating unit 132 monitors a level of the DC voltage converted by the rectifying unit 131. Then, when the DC voltage is greater than or equal to a predetermined threshold value, the activating unit 132 outputs the activation signal.

As described above, the activation signal output unit 53 of the wireless sensing terminal includes the ID demodulating unit 531 and thus outputs the ID matching information to the activating unit 132 only when the received ID information matches the ID information uniquely specifying its own terminal. Further, only when the ID matching information is input from the ID demodulating unit 531, the activating unit 132 monitors the level of the DC voltage converted by the rectifying unit 131. Then, when the monitored DC voltage is greater than or equal to the predetermined threshold value, the activating unit 132 outputs the activation signal. Thus, when the ID information uniquely specifying its own terminal is not received, the wireless sensing terminal does not activate the wireless communication unit 17. Therefore, power consumption can be further reduced, and depletion of a battery can be further suppressed.

Fourth Preferred Embodiment

Next, a fourth preferred embodiment of the present invention will be described with reference to the accompanying drawings. A biological body monitoring system in accordance with the fourth preferred embodiment of the present invention includes a wireless sensing terminal and a data collecting terminal, similarly to the third preferred embodiment. The fourth preferred embodiment of the present invention is different from the third preferred embodiment in a configuration of an activation signal output unit included in the wireless sensing terminal. The remaining configurations of the wireless sensing terminal in the fourth preferred embodiment of the present invention are the same as in the third preferred embodiment. The data collecting terminal in the fourth preferred embodiment of the present invention has the same configuration as the data collecting terminal in the third preferred embodiment.

Figure 8:
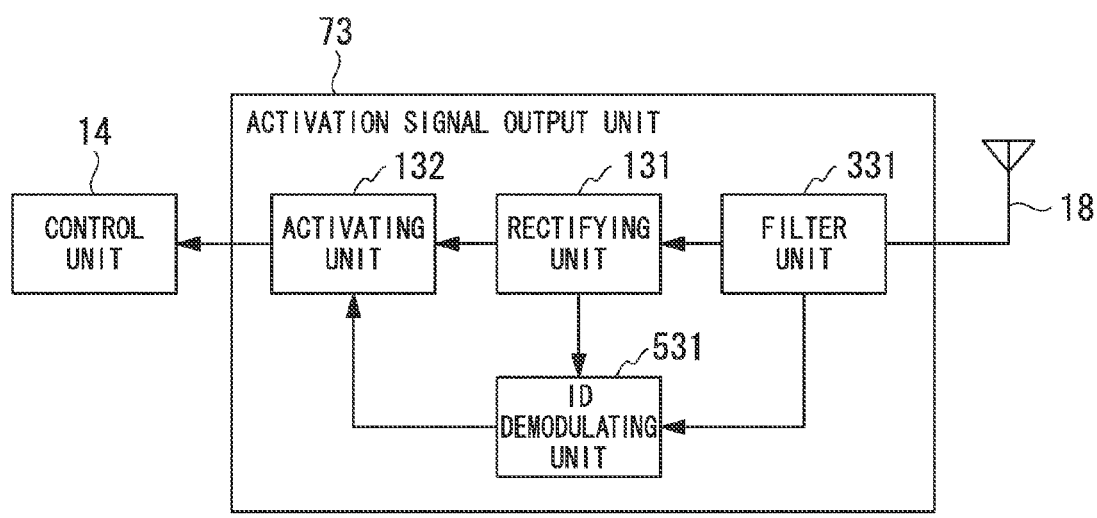
FIG. 8 is a block diagram illustrating a configuration of an activation signal output unit in accordance with a fourth preferred embodiment of the present invention.

Next, a configuration of an activation signal output unit included in the wireless sensing terminal will be described. FIG. 8 is a block diagram illustrating a configuration of an activation signal output unit 73 in accordance with the fourth preferred embodiment of the present invention. In the example of FIG. 8, the activation signal output unit 73 includes a filter unit 331, a rectifying unit 131, an activating unit 132, and an ID demodulating unit 531. The filter unit 331 receives electromagnetic waves transmitted from the outside through the antenna 18, and outputs only an electromagnetic wave of a predetermined frequency band among the received electromagnetic waves to the rectifying unit 131 and the ID demodulating unit 531. The predetermined frequency band includes a frequency band of an electromagnetic wave, which is used to transmit the data request signal and the ID modulation signal, transmitted from the data collecting terminal. Accordingly, it is possible to prevent an electromagnetic wave transmitted from a terminal other than the data collecting terminal from being input to the rectifying unit 131 and the ID demodulating unit 531.

The rectifying unit 131 rectifies the electromagnetic wave input from the filter unit 331 to be converted into a DC voltage, and outputs the converted DC voltage to the activating unit 132 and the ID demodulating unit 531. The activating unit 132 and the ID demodulating unit 531 are the same as in the third preferred embodiment.

As described above, since the activation signal output unit 73 of the wireless sensing terminal includes the filter unit 331, the activation signal output unit 73 can suppress an interference signal or an electromagnetic wave having a frequency band different from a frequency band of the electromagnetic wave used to transmit the data request signal and the ID modulation signal and then demodulate the ID modulation signal.

Further, the activation signal output unit 73 of the wireless sensing terminal includes the ID demodulating unit 531 and thus outputs the ID matching information to the activating unit 132 only when the received ID information matches the ID information uniquely specifying its own terminal. Further, only when the ID matching information is input from the ID demodulating unit 531, the activating unit 132 monitors the level of the DC voltage converted by the rectifying unit 131. Then, when the monitored DC voltage is greater than or equal to the predetermined threshold value, the activating unit 132 outputs the activation signal. Thus, when the ID information uniquely specifying its own terminal is not received, the wireless sensing terminal does not activate the wireless communication unit 17, and so power consumption can be further reduced, and depletion of a battery can be further suppressed.

Fifth Preferred Embodiment

Next, a fifth preferred embodiment of the present invention will be described with reference to the accompanying drawings. A biological body monitoring system in accordance with the fifth preferred embodiment of the present invention includes a wireless sensing terminal and a data collecting terminal, similarly to the fourth preferred embodiment. The fifth preferred embodiment of the present invention is different from the fourth preferred embodiment in the position of a filter unit included in an activation signal output unit. The remaining configurations of the wireless sensing terminal in the fifth preferred embodiment of the present invention are the same as in the fourth preferred embodiment. The data collecting terminal in the fifth preferred embodiment of the present invention has the same configuration as the data collecting terminal in the fourth preferred embodiment.

Figure 9:
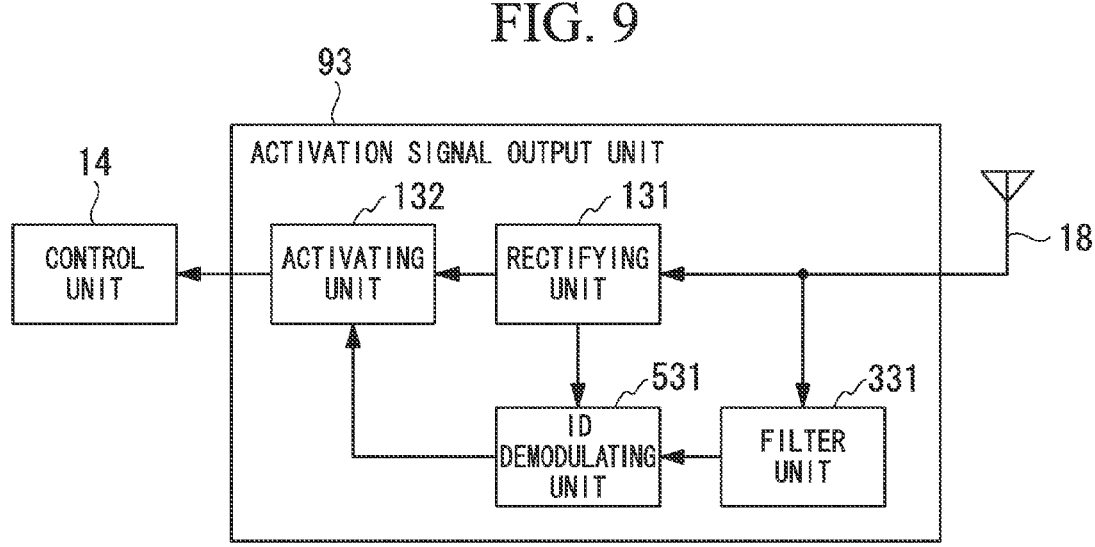
FIG. 9 is a block diagram illustrating a configuration of an activation signal output unit in accordance with a fifth preferred embodiment of the present invention.

Next, a configuration of an activation signal output unit included in the wireless sensing terminal will be described. FIG. 9 is a block diagram illustrating a configuration of an activation signal output unit 93 in accordance with the fifth preferred embodiment of the present invention. In the example of FIG. 9, the activation signal output unit 93 includes a filter unit 331, a rectifying unit 131, an activating unit 132, and an ID demodulating unit 531. The filter unit 331 receives electromagnetic waves transmitted from the outside through the antenna 18, and outputs only an electromagnetic wave of a predetermined frequency band among the received electromagnetic waves to the ID demodulating unit 531. The predetermined frequency band includes a frequency band of an electromagnetic wave, which is used to transmit the data request signal and the ID modulation signal, transmitted from the data collecting terminal. Accordingly, it is possible to prevent an electromagnetic wave transmitted from a terminal other than the data collecting terminal from being input to the ID demodulating unit 531.

The rectifying unit 131 receives the electromagnetic wave transmitted from the data collecting terminal through the antenna 18. The rectifying unit 131 rectifies the received electromagnetic wave to be converted into a DC voltage, and outputs the converted DC voltage to the activating unit 132 and the ID demodulating unit 531. The activating unit 132 and the ID demodulating unit 531 are the same as in the fourth preferred embodiment.

As described above, since the activation signal output unit 93 of the wireless sensing terminal includes the filter unit 331, the activation signal output unit 93 can suppress an interference signal or an electromagnetic wave having a frequency band different from a frequency band of the electromagnetic wave used to transmit the data request signal and the ID modulation signal and then demodulate the ID modulation signal.

Further, the activation signal output unit 93 of the wireless sensing terminal includes the ID demodulating unit 531 and thus outputs the ID matching information to the activating unit 132 only when the received ID information matches the ID information uniquely specifying its own terminal. Further, only when the ID matching information is input from the ID demodulating unit 531, the activating unit 132 monitors the level of the DC voltage converted by the rectifying unit 131. Then, when the monitored DC voltage is greater than or equal to the predetermined threshold value, the activating unit 132 outputs the activation signal. Thus, when the ID information uniquely specifying its own terminal is not received, the wireless sensing terminal does not activate the wireless communication unit 17. Therefore, power consumption can be further reduced, and depletion of a battery can be further suppressed.

Further, in the activation signal output unit 93 of the wireless sensing terminal, the filter unit 331 is not disposed between the antenna 18 and the rectifying unit 131. Thus, the electromagnetic waves including an interference signal or an electromagnetic wave transmitted from a terminal other than the data collecting terminal may be rectified and converted into a DC voltage. Accordingly, more DC voltage may be supplied to the activating unit 132 and the ID demodulating unit 531.

Sixth Preferred Embodiment

Next, a sixth preferred embodiment of the present invention will be described with reference to the accompanying drawings. A biological body monitoring system in accordance with the sixth preferred embodiment of the present invention includes a wireless sensing terminal and a data collecting terminal similarly to the first preferred embodiment. In the first to fifth preferred embodiments, by transmitting the data request signal from the data collecting terminal to the wireless sensing terminal using the electromagnetic wave, the wireless communication unit of the wireless sensing terminal is activated. However, in a sixth preferred embodiment of the present invention, by transmitting the collection data from the wireless sensing terminal to the data collecting terminal using the electromagnetic wave, the wireless communication unit of the data collecting terminal is activated.

Figure 10:
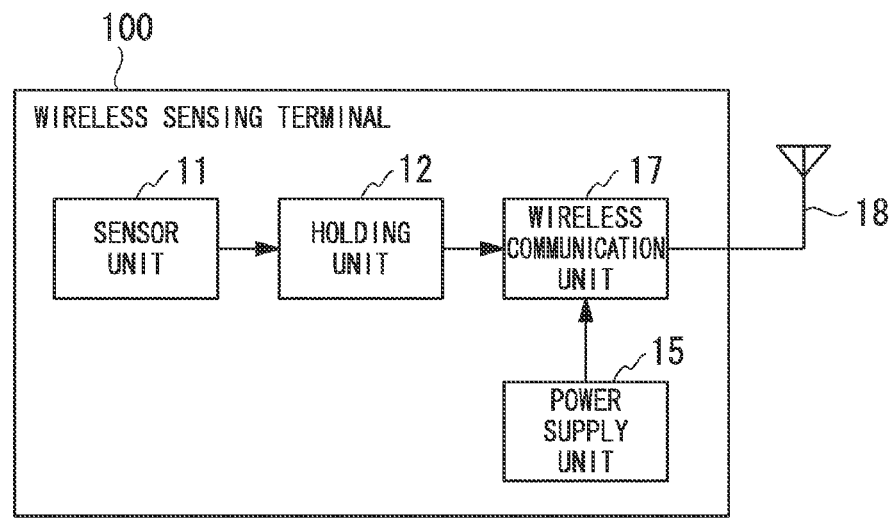
FIG. 10 is a block diagram illustrating a configuration of a wireless sensing terminal in accordance with a sixth preferred embodiment of the present invention.

Next, a configuration of the wireless sensing terminal will be described. FIG. 10 is a block diagram illustrating a configuration of a wireless sensing terminal 100 in accordance with the sixth preferred embodiment of the present invention. In the example of FIG. 10, the wireless sensing terminal 100 includes a sensor unit 11, a holding unit 12, a power supply unit 15, a wireless communication unit 17, and an antenna 18.

The sensor unit 11 is the same as the sensor unit 11 in the first preferred embodiment. The holding unit 12 acquires and holds the collection data output from the sensor unit 11, and outputs the held collection data to the wireless communication unit 17. The wireless communication unit 17 transmits the collection data to the data collecting terminal through the antenna 18 using an electromagnetic wave. The wireless communication unit 17 may transmit the collection data to the wireless sensing terminal at an arbitrary timing such as a timing instructed by a user or a predetermined timing.

Figure 11:
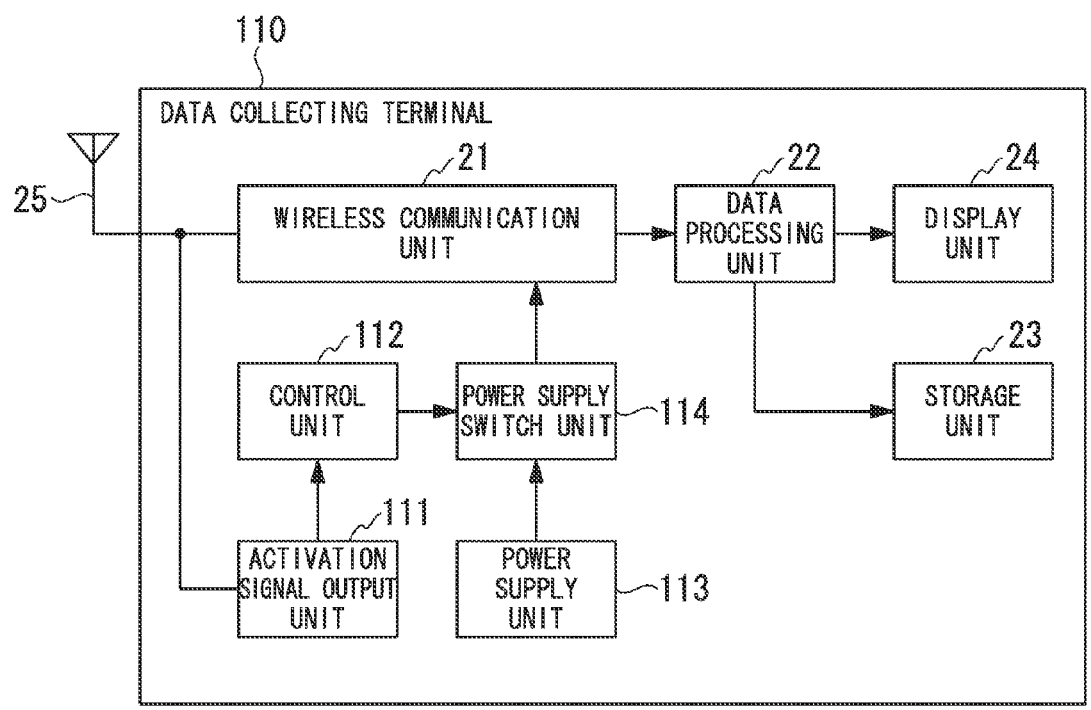
FIG. 11 is a block diagram illustrating a configuration of the data collecting terminal in accordance with the sixth preferred embodiment of the present invention.

Next, a configuration of a data collecting terminal 110 will be described. FIG. 11 is a block diagram illustrating a configuration of the data collecting terminal 110 in accordance with the sixth preferred embodiment of the present invention. In the example of FIG. 11, the data collecting terminal 110 includes a wireless communication unit 21 (a wireless communication module), a data processing unit 22, a storage unit 23, a display unit 24, an antenna 25 (a wireless communication antenna), an activation signal output unit 111, a control unit 112, a power supply unit 113, and a power supply switch unit 114.

The activation signal output unit 111 rectifies an electromagnetic wave transmitted from the wireless sensing terminal 100 through the antenna 25 to be converted into a DC voltage. When the converted DC voltage is greater than or equal to a predetermined threshold value, the activation signal output unit 111 generates an activation signal and outputs the activation signal to the control unit 112. When the activation signal is input from the activation signal output unit 111, the control unit 112 controls the power supply switch unit 114 such that electric power is supplied from the power supply unit 113 to the wireless communication unit 21. After the wireless communication unit 21 completes reception of data, the control unit 112 controls the power supply switch unit 114 such that a supply of electric power from the power supply unit 113 to the wireless communication unit 21 is stopped.

The power supply unit 113 supplies electric power to the wireless communication unit 21 under control of the power supply switch unit 114. The power supply switch unit 114 controls a supply of electrical power from the power supply unit 113 to the wireless communication unit 21 under control of the control unit 112. The wireless communication unit 21 is supplied with electrical power from the power supply unit 113 and then activated (starts its operation). The wireless communication unit 21 receives the collection data transmitted from the wireless sensing terminal 100 using the electromagnetic wave through the antenna 25. The wireless communication unit 21 outputs the received collection data to the data processing unit 22. The data processing unit 22, the storage unit 23, and the display unit 24 are the same as in the first preferred embodiment.

As described above, the activation signal output unit 111 of the data collecting terminal 110 rectifies the electromagnetic wave transmitted from the wireless sensing terminal 100 to be converted into the DC voltage. Further, when the converted DC voltage is greater than or equal to a predetermined threshold value, the activation signal output unit 111 outputs the activation signal. Further, when the activation signal output unit 111 outputs the activation signal, the control unit 112 controls the power supply switch unit 114 such that electric power is supplied from the power supply unit 113 to the wireless communication unit 21. Further, the wireless communication unit 21 is supplied with electrical power from the power supply unit 113 and then activated (starts its operation). Further, the wireless communication unit 21 receives the collection data transmitted from the wireless sensing terminal 100 using electric power supplied from the power supply unit 113. Further, after the wireless communication unit 21 completes reception of the collection data, the control unit 112 stops a supply of electric power from the power supply unit 113 to the wireless communication unit 21. Further, when a supply of electric power from the power supply unit 113 is stopped, the wireless communication unit 21 stops its operation.

As described above, the data collecting terminal 110 generates the activation signal from the electromagnetic wave, which is used to transmit the collection data, transmitted from the wireless sensing terminal 100. Then, the data collecting terminal 110 supplies electric power to the wireless communication unit 21 based on the generated activation signal and thereby activates the wireless communication unit 21. Accordingly, the data collecting terminal 110 can activate the wireless communication unit 21 when communication is started while further reducing power consumption. Further, since the data collecting terminal 110 activates the wireless communication unit 21 when communication is started, power consumption at the time of standby can be reduced, and depletion of the power supply unit 113 can be suppressed.

While preferred embodiments of the present invention have been described and illustrated above, it should be understood that these are examples of the present invention and are not to be considered as limiting. Additions, omissions, substitutions, and other modifications can be made without departing from the scope of the present invention.

For example, in the first to sixth preferred embodiments, the wireless sensing terminal and the data collecting terminal perform wireless communication in a one-to-one manner. However, the present invention can be applied even when the wireless sensing terminal and the data collecting terminal perform wireless communication in a 1-to-N manner, an M-to-1 manner, or an M-to-N manner (N and M are natural numbers).

Accordingly, the present invention is not to be considered as being limited by the foregoing description, and is only limited by the scope of the claims.

What is claimed is:

1. A wireless communication terminal comprising:
   a battery that supplies a first direct current (DC) power;
   a wireless communication antenna;
   a wireless communication module that transmits communication data to an external terminal through the wireless communication antenna;
   an activation signal output unit that converts an electromagnetic wave received through the wireless communication antenna into a second direct current (DC) power, and generates and outputs an activation signal if the converted second DC power is greater than or equal to a predetermined power value; and
   a control unit that performs control such that the first DC power is supplied from the battery to the wireless communication module if the activation signal is output from the activation signal output unit,
   wherein only the first DC power is used power the wireless communication module.

2. The wireless communication terminal according to claim 1, wherein the activation signal output unit comprises a rectifying unit that converts the electromagnetic wave into the second DC power through rectification, and the activation signal output unit outputs the activation signal if the second DC power converted by the rectifying unit is greater than or equal to a predetermined value.

3. The wireless communication terminal according to claim 2, wherein the activation signal output unit further comprises a filter unit that extracts only an electromagnetic wave of a specific frequency band from the electromagnetic wave, and the rectifying unit rectifies only the extracted electromagnetic wave of the frequency band, and outputs the activation signal if the second DC power of only the extracted electromagnetic wave of the frequency band becomes greater than or equal to a predetermined power value.

4. The wireless communication terminal according to claim 3, wherein the activation signal output unit further comprises a demodulating unit that demodulates an identifier transmitted by using the electromagnetic wave, and the activation signal output unit outputs the activation signal only when the identifier demodulated by the demodulating unit is a predetermined identifier.

5. The wireless communication terminal according to claim 4, wherein the demodulating unit operates by using the second DC power converted by the rectifying unit.

6. The wireless communication terminal according to claim 2, wherein the activation signal output unit further comprises a demodulating unit that demodulates an identifier transmitted by using the electromagnetic wave, and the activation signal output unit outputs the activation signal if the identifier demodulated by the demodulating unit is a predetermined identifier.

7. The wireless communication terminal according to claim 6, wherein the demodulating unit operates by using the second DC power converted by the rectifying unit.

8. The wireless communication terminal according to claim 1, wherein the wireless communication terminal is a terminal installed inside a body.

9. The wireless communication terminal according to claim 1, wherein the wireless communication terminal is a terminal installed outside a body.

10. The wireless communication terminal according to claim 1, wherein the control unit controls such that a supply of the first DC power from the battery to the wireless communication module is stopped after the wireless communication module completes data transmission of the communication data to the external terminal.

* * * * *